(12) United States Patent
Hodges et al.

(10) Patent No.: US 8,597,480 B2
(45) Date of Patent: *Dec. 3, 2013

(54) ELECTROCHEMICAL CELL

(75) Inventors: Alastair McIndoe Hodges, Blackburn South (AU); Thomas William Beck, North Richmond (AU); Oddvar Johansen, Mulgrave (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/357,318

(22) Filed: Jan. 24, 2012

(65) Prior Publication Data

US 2012/0145539 A1    Jun. 14, 2012

Related U.S. Application Data

(63) Continuation of application No. 12/567,433, filed on Sep. 25, 2009, now Pat. No. 8,101,056, which is a continuation of application No. 10/624,795, filed on Jul. 22, 2003, now Pat. No. 7,608,175, which is a continuation of application No. 10/035,924, filed on Dec. 21, 2001, now Pat. No. 6,960,289, which is a continuation of application No. 09/618,515, filed on Jul. 18, 2000, now Pat. No. 6,413,410, which is a continuation of application No. 08/981,385, filed as application No. PCT/AU96/00365 on Jun. 19, 1996, now Pat. No. 6,284,125.

(30) Foreign Application Priority Data

Jun. 19, 1995   (AU) ........................................ PN 3639

(51) Int. Cl.
  *G01N 27/403*   (2006.01)
  *G01N 27/327*   (2006.01)
(52) U.S. Cl.
  USPC ..................... 204/400; 204/403.03

(58) Field of Classification Search
  USPC ....................... 204/403.01–402.15, 400, 242; 205/777.5, 778, 792
  See application file for complete search history.

(56) References Cited

U.S. PATENT DOCUMENTS

| 4,053,381 A | 10/1977 | Hamblen et al. |
| 4,076,596 A | 2/1978 | Connery et al. |

(Continued)

FOREIGN PATENT DOCUMENTS

| AU | 54873/94 | 2/1993 |
| AU | 5487394 | 2/1993 |

(Continued)

OTHER PUBLICATIONS

Osamu, Niwa, et al. "Electrochemical Behavior of Reversible Redox Species at Interdigitated Array Electrodes with Different Geometries: Consideration of Redox Cycling and Collection Efficiency", Analytical Chemistry; Mar. 1990, vol. 62, No. 5, pp. 447-452.

(Continued)

*Primary Examiner* — Alex Noguerola
(74) *Attorney, Agent, or Firm* — Hiscock & Barclay, LLP

(57) ABSTRACT

Devices and methods are provided for determining the concentration of a reduced form of a redox species. For example, a device can include a working electrode and a counter electrode spaced by a predetermined distance so that reaction produces from the counter electrode arrive at the working electrode. An electric potential difference can be applied between the electrodes, and the potential of the working electrode can be selected such that the rate of electro-oxidation of the reduced form of the species is diffusion controlled. Current as a function of time can be determined, the magnitude of the steady state current can be estimated, and a value indicative of the diffusion coefficient and/or of the concentration of the reduced form of the species can be obtained from the change in current with time and the magnitude of the steady state current. Other embodiments of apparatuses, devices, and methods are also provided.

7 Claims, 5 Drawing Sheets

(56) References Cited

U.S. PATENT DOCUMENTS

| | | | |
|---|---|---|---|
| 4,088,448 A | 5/1978 | Lilja et al. | |
| 4,224,125 A | 9/1980 | Nakamura et al. | |
| 4,233,029 A | 11/1980 | Columbus | |
| 4,254,083 A | 3/1981 | Columbus | |
| 4,254,546 A | 3/1981 | Ullery, Jr. | |
| 4,259,165 A | 3/1981 | Miyake | |
| 4,301,412 A | 11/1981 | Hill et al. | |
| 4,301,414 A | 11/1981 | Hill et al. | |
| 4,303,887 A | 12/1981 | Hill et al. | |
| 4,307,188 A | 12/1981 | White | |
| 4,319,969 A | 3/1982 | Oda et al. | |
| 4,374,013 A | 2/1983 | Enfors | |
| 4,404,065 A | 9/1983 | Matson | 205/780.5 |
| 4,404,066 A | 9/1983 | Johnson | |
| 4,431,004 A | 2/1984 | Bessman et al. | |
| 4,431,507 A | 2/1984 | Nankai et al. | |
| 4,508,613 A | 4/1985 | Busta et al. | |
| 4,511,659 A | 4/1985 | Matson | 205/780.5 |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,552,840 A | 11/1985 | Riffer | |
| 4,554,064 A | 11/1985 | McClintock et al. | 204/411 |
| 4,591,550 A | 5/1986 | Hafeman et al. | |
| 4,629,563 A | 12/1986 | Wrasidlo | |
| 4,654,197 A | 3/1987 | Lilja et al. | |
| 4,664,119 A | 5/1987 | Bessman et al. | |
| 4,711,245 A | 12/1987 | Higgins et al. | 204/403.1 |
| 4,774,039 A | 9/1988 | Wrasidlo | |
| 4,782,265 A | 11/1988 | Schaper et al. | |
| 4,790,925 A | 12/1988 | Miller et al. | |
| 4,897,173 A | 1/1990 | Nankai et al. | |
| 4,900,424 A | 2/1990 | Birth et al. | |
| 4,911,794 A | 3/1990 | Parce et al. | |
| 4,919,770 A | 4/1990 | Preidel et al. | |
| 4,963,815 A | 10/1990 | Hafeman | |
| 4,988,429 A | 1/1991 | Matthiessen | |
| 4,989,452 A | 2/1991 | Toon et al. | |
| 5,059,908 A | 10/1991 | Mina | |
| 5,064,516 A | 11/1991 | Rupich | |
| 5,089,112 A | 2/1992 | Skotheim et al. | |
| 5,089,320 A | 2/1992 | Straus et al. | 428/216 |
| 5,095,407 A | 3/1992 | Kanezawa et al. | |
| 5,108,564 A | 4/1992 | Szuminsky et al. | 205/777.5 |
| 5,120,420 A | 6/1992 | Nankai et al. | |
| 5,122,244 A | 6/1992 | Hoenes et al. | |
| 5,126,034 A | 6/1992 | Carter et al. | 204/403.05 |
| 5,128,015 A | 7/1992 | Szuminsky et al. | |
| 5,141,868 A | 8/1992 | Shanks et al. | |
| 5,151,166 A | 9/1992 | Harral et al. | |
| 5,156,972 A | 10/1992 | Issachar | |
| 5,171,689 A | 12/1992 | Kawaguri et al. | 204/403.1 |
| 5,192,415 A | 3/1993 | Yoshioka et al. | 204/403.08 |
| 5,194,133 A * | 3/1993 | Clark et al. | 204/608 |
| 5,229,282 A | 7/1993 | Yoshioka et al. | |
| 5,243,516 A | 9/1993 | White | 435/287.2 |
| 5,243,526 A | 9/1993 | Ito et al. | |
| 5,269,903 A | 12/1993 | Ikariyama et al. | |
| 5,272,087 A | 12/1993 | El Murr et al. | |
| 5,282,950 A | 2/1994 | Dietze et al. | |
| 5,288,636 A | 2/1994 | Pollmann et al. | |
| 5,312,590 A | 5/1994 | Gunasingham | |
| 5,314,605 A | 5/1994 | Matthiessen et al. | |
| 5,320,732 A | 6/1994 | Nankai et al. | |
| 5,354,447 A | 10/1994 | Uenoyama et al. | |
| 5,366,609 A | 11/1994 | White et al. | |
| 5,382,346 A | 1/1995 | Uenoyama et al. | |
| 5,384,028 A | 1/1995 | Ito | |
| 5,385,846 A | 1/1995 | Kuhn et al. | 205/777.5 |
| 5,388,163 A | 2/1995 | Elko et al. | |
| 5,393,399 A | 2/1995 | Van den Berg et al. | |
| 5,395,504 A | 3/1995 | Saurer et al. | |
| 5,399,256 A | 3/1995 | Bohs et al. | |
| 5,405,511 A | 4/1995 | White et al. | 205/777.5 |
| 5,413,690 A | 5/1995 | Kost et al. | |
| 5,437,999 A | 8/1995 | Diebold et al. | 204/403.11 |
| 5,443,710 A | 8/1995 | Broderick | 204/403.13 |
| 5,496,453 A | 3/1996 | Uenoyama et al. | |
| 5,508,171 A | 4/1996 | Walling et al. | |
| 5,509,410 A | 4/1996 | Hill et al. | |
| 5,512,159 A | 4/1996 | Yoshioka et al. | |
| 5,517,313 A | 5/1996 | Colvin, Jr. | |
| 5,518,590 A | 5/1996 | Fang | |
| 5,520,787 A | 5/1996 | Hanagan et al. | 204/403.14 |
| 5,527,446 A | 6/1996 | Kosek et al. | |
| 5,567,302 A | 10/1996 | Song et al. | |
| 5,575,895 A | 11/1996 | Ikeda et al. | |
| 5,607,565 A | 3/1997 | Azarnia et al. | |
| 5,611,908 A | 3/1997 | Matthiessen et al. | |
| 5,620,579 A | 4/1997 | Genshaw et al. | |
| 5,628,890 A | 5/1997 | Carter et al. | |
| 5,645,709 A | 7/1997 | Birch et al. | |
| 5,651,869 A | 7/1997 | Yoshioka et al. | |
| 5,682,884 A | 11/1997 | Hill et al. | |
| 5,695,947 A | 12/1997 | Guo et al. | |
| 5,707,502 A | 1/1998 | McCaffrey et al. | |
| 5,726,565 A | 3/1998 | Uchiyama et al. | |
| 5,727,548 A | 3/1998 | Hill et al. | |
| 5,762,770 A | 6/1998 | Pritchard et al. | 204/403.14 |
| 5,849,174 A | 12/1998 | Sanghera et al. | |
| 5,858,188 A | 1/1999 | Soane et al. | 204/454 |
| 5,863,400 A | 1/1999 | Drummond et al. | |
| 5,909,114 A | 6/1999 | Uchiyama et al. | |
| 5,942,102 A | 8/1999 | Hodges et al. | |
| 5,997,817 A | 12/1999 | Crismore et al. | |
| 6,071,391 A | 6/2000 | Gotoh et al. | |
| 6,117,289 A | 9/2000 | Yamamoto et al. | |
| 6,153,069 A | 11/2000 | Pottgen et al. | 204/403.11 |
| 6,174,420 B1 | 1/2001 | Hodges et al. | |
| 6,179,979 B1 | 1/2001 | Hodges et al. | |
| 6,193,873 B1 | 2/2001 | Ohara et al. | |
| 6,214,205 B1 | 4/2001 | Willner et al. | |
| 6,218,134 B1 | 4/2001 | Yamauchi et al. | |
| 6,251,260 B1 | 6/2001 | Heller et al. | |
| 6,270,637 B1 | 8/2001 | Crismore et al. | |
| 6,284,125 B1 | 9/2001 | Hodges et al. | 205/775 |
| 6,325,973 B1 | 12/2001 | Leland et al. | |
| 6,413,395 B1 | 7/2002 | Bhullar et al. | |
| 6,413,410 B1 | 7/2002 | Hodges et al. | 205/775 |
| 6,461,496 B1 | 10/2002 | Feldman et al. | |
| 6,503,381 B1 | 1/2003 | Gotoh et al. | |
| 6,521,110 B1 | 2/2003 | Hodges et al. | |
| 6,544,212 B2 | 4/2003 | Galley et al. | |
| 6,780,756 B1 | 8/2004 | Farber et al. | |
| 6,863,801 B2 | 3/2005 | Hodges et al. | |
| 7,431,814 B2 | 10/2008 | Hodges et al. | |
| 7,604,722 B2 | 10/2009 | Hodges et al. | |
| 7,608,175 B2 * | 10/2009 | Hodges et al. | 204/403.02 |
| 8,101,056 B2 * | 1/2012 | Hodges et al. | 204/400 |
| 2002/0012943 A1 | 1/2002 | Fowlkes et al. | |

FOREIGN PATENT DOCUMENTS

| | | |
|---|---|---|
| AU | 31042/93 | 7/1993 |
| AU | 3104293 | 7/1993 |
| AU | 3104293 A | 7/1993 |
| AU | 54873/94 B2 | 8/1994 |
| AU | 5487394 A | 8/1994 |
| CN | 1325908 | 12/2001 |
| DE | 3103-464 | 8/1982 |
| DE | 3103 464 A1 | 8/1982 |
| DE | 3103464 | 8/1982 |
| DE | 3103464 A1 | 8/1982 |
| DE | 3103464 A1 | 8/1982 |
| DE | 3103484 | 8/1982 |
| DE | 29709141 | 8/1997 |
| EP | 0125 137 A2 | 11/1984 |
| EP | 0125137 A2 | 11/1984 |
| EP | 0127958 A2 | 12/1984 |
| EP | 170375 A2 | 2/1986 |
| EP | 0171375 A1 | 2/1986 |
| EP | 0 251 915 A2 | 1/1988 |
| EP | 0251915 A2 | 1/1988 |

(56) References Cited

FOREIGN PATENT DOCUMENTS

| | | |
|---|---|---|
| EP | 0 255 291 A1 | 2/1988 |
| EP | 0255291 A1 | 2/1988 |
| EP | 0 266 204 A2 | 4/1988 |
| EP | 0266204 A2 | 5/1988 |
| EP | 0 278 647 A2 | 8/1988 |
| EP | 0278647 A2 | 8/1988 |
| EP | 0290770 | 11/1988 |
| EP | 0290770 A2 | 11/1988 |
| EP | 0 299 779 A2 | 1/1989 |
| EP | 0299779 A2 | 1/1989 |
| EP | 0 351 516 A2 | 1/1990 |
| EP | 0 351 891 | 1/1990 |
| EP | 0 351 892 A2 | 1/1990 |
| EP | 0351516 A2 | 1/1990 |
| EP | 0351892 A2 | 1/1990 |
| EP | 0 359 831 | 3/1990 |
| EP | 0 171 375 A1 | 5/1990 |
| EP | 0 367 432 | 5/1990 |
| EP | 0 367 432 A1 | 5/1990 |
| EP | 0170 375 | 5/1990 |
| EP | 0367432 A1 | 5/1990 |
| EP | 0 400 918 A1 | 12/1990 |
| EP | 0400918 | 12/1990 |
| EP | 0406304 A1 | 1/1991 |
| EP | 0 418 404 A1 | 3/1991 |
| EP | 0418404 A1 | 3/1991 |
| EP | 0 422 708 | 4/1991 |
| EP | 0 451 981 A2 | 10/1991 |
| EP | 0451981 A2 | 10/1991 |
| EP | 0 127 958 B2 | 3/1992 |
| EP | 0 560 336 A1 | 9/1993 |
| EP | 0560336 A1 | 9/1993 |
| EP | 0 585 933 | 3/1994 |
| EP | 593096 A2 | 4/1994 |
| EP | 593096 A2 | 4/1994 |
| EP | 0 603 954 | 6/1994 |
| EP | 0 609 760 A1 | 8/1994 |
| EP | 0609760 A1 | 8/1994 |
| EP | 0 735 303 A1 | 10/1996 |
| EP | 0735303 A1 | 10/1996 |
| EP | 0 741 186 | 11/1996 |
| EP | 0 764 469 | 3/1997 |
| EP | 0 406 304 B1 | 8/1997 |
| EP | 0 964 059 | 12/1999 |
| GB | 2 020 424 | 11/1979 |
| GB | 2020424 A | 11/1979 |
| GB | 2020424 A | 11/1979 |
| GB | 2 154 735 A | 9/1985 |
| GB | 2154735 A | 9/1985 |
| GB | 2194112 | 2/1988 |
| GB | 2 201 248 A | 8/1988 |
| GB | 2201248 A | 8/1988 |
| GB | 2215846 | 9/1989 |
| GB | 2215846 A | 9/1989 |
| GB | 2 235 050 A | 2/1991 |
| GB | 2235050 A | 2/1991 |
| JP | 54006595 | 1/1979 |
| JP | 60017344 | 1/1985 |
| JP | 60244853 | 12/1985 |
| JP | 60250246 | 12/1985 |
| JP | 61002060 | 1/1986 |
| JP | 62 22874 | 10/1987 |
| JP | 6222874 | 10/1987 |
| JP | 62228274 | 10/1987 |
| JP | 63-317097 A | 12/1988 ............... C12Q 1/00 |
| JP | 01253648 | 10/1989 |
| JP | 01294453 | 11/1989 |
| JP | 3107747 A | 5/1991 |
| JP | 3 167484 | 7/1991 |
| JP | 3167464 | 7/1991 |
| JP | 3167464 A | 7/1991 |
| JP | 4062463 A | 2/1992 |
| JP | 4 66112 A | 3/1992 |
| JP | 466112 A | 3/1992 |
| JP | 466112 A | 3/1992 |
| JP | 4-343065 | 11/1992 |
| JP | 04-343065 A | 11/1992 |
| JP | 4340453 A | 11/1992 |
| JP | 4340453 A | 11/1992 |
| JP | 04343065 A | 11/1992 |
| JP | 04343065 A | 11/1992 |
| JP | 5- 2007 | 1/1993 |
| JP | 05-2007 | 1/1993 |
| JP | 05002007 | 1/1993 |
| JP | 0580018 | 3/1993 |
| JP | 5256812 A | 10/1993 |
| JP | 05-312761 | 11/1993 |
| JP | 5312760 A | 11/1993 |
| JP | 5312760 A | 11/1993 |
| JP | 5312761 A | 11/1993 |
| JP | 6150262 A | 5/1994 |
| JP | 6222874 | 8/1994 |
| JP | 6224140 A | 8/1994 |
| JP | 06310746 | 11/1994 |
| JP | 8062179 A | 3/1996 |
| JP | 08304340 | 11/1996 |
| JP | 9222408 | 8/1997 |
| JP | 9236570 | 9/1997 |
| JP | 9243588 | 9/1997 |
| JP | 2001281219 A | 10/2001 |
| JP | 2007225619 | 9/2007 |
| RU | 2 046 361 C1 | 10/1995 |
| RU | 2 046 361 C1 | 10/1995 |
| SU | 1351-627 A | 11/1987 |
| SU | 1351627 | 11/1987 |
| SU | 1351627 A | 11/1987 |
| SU | 1806187 | 3/1993 |
| WO | WO 89/08713 | 9/1989 |
| WO | WO-8908713 A1 | 9/1989 |
| WO | 9005910 | 5/1990 |
| WO | WO-9005910 A1 | 5/1990 |
| WO | 9109139 | 6/1991 |
| WO | WO-9109139 A1 | 6/1991 |
| WO | WO 92/15701 | 9/1992 |
| WO | WO-9215701 A1 | 9/1992 |
| WO | WO 94/02842 | 2/1994 |
| WO | WO-9402842 A1 | 2/1994 |
| WO | WO 94/29731 | 12/1994 |
| WO | WO 94/29731 A1 | 12/1994 |
| WO | WO-9429731 A1 | 12/1994 |
| WO | WO 95/16198 | 6/1995 |
| WO | WO-9516198 A1 | 6/1995 |
| WO | 9521934 | 8/1995 |
| WO | WO-9521934 | 8/1995 |
| WO | WO-9528634 A1 | 10/1995 |
| WO | WO 97/00441 | 1/1997 |
| WO | WO-9700441 A1 | 1/1997 |
| WO | 9718464 | 5/1997 |
| WO | 9718465 | 5/1997 |
| WO | WO-9718464 | 5/1997 |
| WO | WO-9718465 | 5/1997 |
| WO | 9811426 | 3/1998 |
| WO | WO-9811426 | 3/1998 |
| WO | 9843073 | 10/1998 |
| WO | 9843074 | 10/1998 |
| WO | WO-9843073 | 10/1998 |
| WO | WO-9843074 | 10/1998 |
| WO | 9946585 | 9/1999 |
| WO | WO-9946585 | 9/1999 |
| WO | 0020626 | 4/2000 |
| WO | WO-0020626 | 4/2000 |
| WO | 0208763 | 1/2002 |
| WO | WO-0208763 | 1/2002 |

OTHER PUBLICATIONS

Jung and Kwak; "Simultaneous Determination of Diffusion Coefficient and Concentration by Chronoamperometry at a Microdisk Electrode"; *Bull Korean Chem. Soc.*; 1004, V. 15, No. 3, pp. 209-213.

Specification sheet from Adhesives Research, Inc., ARClad®8314 (May 2, 1997) (1 pg.).

Specification sheet from Adhesives Research, Inc., ARCare®7148, double-sided adhesive coated polyester film (Mar. 30, 1995) (2 pages).

(56) References Cited

OTHER PUBLICATIONS

Oglesby, Omang, and Reilley; "*Thin Layer Electrochemical Studies Using Controlled Potential or Controlled Current*", Analytical Chemistry, vol. 37, No. 11, Oct. 1965, pp. 1312-1316.
Derwent Abstract Accession No. 93-140898/17, class S03, JP, A., 05080018 (Rikagaku Kenkyusho) Mar. 30, 1993.
Derwent Abstract No. 95-026336/04, class S03, JP, A., 06310746 (Hitachi Ltd) Nov. 4, 1994.
Anderson et al., "Diagnostic Criteria for the Study of Chemical and Physical Processes by Twin-Electrode Thin-Layer Electrochemistry"; *J. Electroanal.Chem.*, 12 (1996)477-494.
Patent Abstract of Japan JP-04-56112-A.
Daruhazi, et al., "Cyclic Voltammetry for Reversible Redox-Electrode Reaction in Thin Layer Cells with Closely Separated Working and Auxiliary Electrodes of the Same Size", in J. Electroanal. Chem. 264; 77-89 (1989).
Denuault, et al., Direct Determination of Diffusion-Coefficients by Chronoamperometry at Microdisk Electrodes, Journal of Electroanalytical Chemistry, vol. 308, No. 1-2, 1991, pp. 27-38.
European Search Report for App. No. 96 93 7919.
European Search Report for App. No. 99 20 2305.
Hall, E., Biosensors, Chapter 5: "Amperometric Assay Techniques", 1990.
International Search Report PCT/US02/31289 dated Jul. 18, 2003.
O. Niwa, M. Morita, H. Tabei, "Highly Selective Electrochemical Detection of Dopamine Using Interdigitated Array of Electrodes Modified with Nafron (sp?) Polyester Ionomer Layered Film", Electroanalysis, vol. 6, No. 3, Mar. 1994, pp. 237-243, XP000943528.
Paeschke, et al., "Dynamic Redox Recycling of Cytochrome C", Journal of Electroanalytical Chemistry; vol. 393, No. 1/02, 1995, pp. 131-135.
Salbeck, J., Spectrochemical Thin-Layer Cell for Nonaqueous Solvent Systems, Anal. Chem., 1993, vol. 65, pp. 2165-2173.
Seddon, et al., Preparation and Amperometric Response of Carbon and Platinum Dual Cylinder Microelectrodes, Electrochimica Acta, vol. 40, No. 4, Mar. 1, 1995, pp. 455-465.
Trojanek, et al., Data processing in reaction rate measurements, Collect. Chzech. Chem commun., 38(9)2572-2580, 1973.
Uchiyama, et al., Measurement of Homogeneous Reaction Rate by Concentration-Step, Controlled Potential Electrolysis, J. Electroanal. Chem Interfacial Electrochem., 91(3):301-308, 1978.
Yaoita, et al., Pulse Chronoamperometric Technique of Enzyme Embodied Electrode Applied to Glucose Measurement in Whole Serum, Extended Abstracts, US, Electrochemical Society, Princeton, NJ; vol. 93/1, 1993, p. 2801.
Vidal, J.C. et al., "A Chronoamperometric Sensor for Hydrogen Peroxide Based on Electron Transfer Between Immobilized Horseradish Peroxidase on a Glassy Carbon Electrode and a Diffusing Ferrocene Mediator", Sensors and Actuators B:Chemical, vol. 21, Issue 2, Aug. 1994, pp. 135-141.
Chinese Office Action (Application No. CN200610100717.9) dated Dec. 5, 2008.
"Enthone-Imaging Technologies Update" Jun. 2001/No. 3.
European Search Report No. EP 03 00 7604 dated May 19, 2003.
Patent Abstracts of Japan, JP A 04-62463.
Patent Abstracts of Japan, JP 1 59-3345, p-269, p. 166 (Hitachi Seisakusho KK.) Jan. 10, 1994.
Hubbard, et al. The Theory and Practice of Electrochemistry with Thin Layer Cells, in *Electroanalytical Chemistry*, (Bard, Ed.), Marcel Deletier New York, 1970< vol. 4 (pp. 129-214). *B.*
Japanese Patent Abstract JP63-139246 A2 (Jun. 1988).
Patent Abstracts of Japan, JP 0 05312761 A2; 1993; Y. Fukuda, et al.
Cassedy, et al. "Novel Electrochemical Device for the Detection of Cholesterol or Glucose", Analyst, vol. 118; Apr. 1993; pp. 415-418.
Christensen & Anson: "Chronopentrometry in Thin Layers of Solution", Analytical Chemistry, vol. 35; No. 2, 1963, pp. 205-209.
Hubbard & Anson; "New Elecrodes for Chronopotentiometry in Thin Layers of Solution", Analytical Chemistry, vol. 36, No. 4, Apr. 1964, pp. 723-728.

McDuffie, Anderson, & Reilley; "Twin Electrode Thin-Layer Electrochemistry", Analytical Chemistry, vol. 38, No. 7, Jun. 1966; pp. 883-890.
Nicholson and Shah "Theory of Stationary Electrode Polaroarography", Analytical Chemistry: vol. 36, No. 4, Apr. 1964, pp. 706-723.
Pickup, Kutner, Leidner, and Murray, Redox Conduction in single and Bilayer Films of Redox Polymer, J. Amer. Chem. Soc.; vol. 106; No. 7; 1984.
Chidsey, Feldman, Lundgren, and Murray; "Micrometer-Spaced Platinum Interdigitated Array Electrode: Febrication, Theory, and Initial Use", Analytical Chemistry, vol. 58, No. 3, Mar. 1986, pp. 801-807.
Hubbard, "Study of the Kinetics of Electrochemical Reactions by Thin-Layer Voitammetry"; J. Electroanalytical Chemistry, vol. 22, 1969, pp. 165-174.
Anderson and Reilley; "Thin-Layer Electrochemistry: Steady-State Methods of Studying Rate Processes"; J. Electroanalytical Chemistry, vol. 10, 1965, pp. 295-305.
Patent Abstracts of Japan, JP 08062179A; Electrolyte Analyzer, (Mar. 8, 1996).
Reilley, Charles; "Electrochemistry Using Thin-Layer Cells", Review of Pure and Appl. Chem, vol. 18, 1968, pp. 137-151.
Morris, Franta and White; "Electrochemistry at Pt Band Electrodes of Width Approaching Molecular Dimensions, Breakdown of Transport Equations at Very Small Electrodes", J. of Physical Chemistry, vol. 91, No. 13, 1987, pp. 3559-3564.
Paeschke, e al., Properties of Interdigital Electrode Arrays With Different Geometries, Analytical Chimica Acta; vol. 305, No. 1/03, 1995, pp. 126-136.
Japanese Office Action (Application No. 102675/2007) dated Jan. 8, 2010.
Denuault et al., Direct Determination of Diffusion-Coefficients by Chronoamperometry at Microdisk Electrodes, Journal of Electroanalytical Chemistry, vol. 308, No. 1-2, 1991, pp. 27-38.
Paeschke, et al., "Properties of Interdigital Electrode Arrays With Different Geometries", Analytica Chimica Acta; vol. 305, No. 1/03, 1995, pp. 126-136.
Trojanek, et al., Data processing in reaction rate measurements, Collect. Chzech. Chem commun., 38(9):2572-2580, 1973.
Yaoita, M. et al., "Pulse Chronoamperometric Technique of Enzyme Embodied Electrode Applied to Glucose Measurement in Whole Serum", Extended Abstracts, US, Electrochemical Society, Princeton, NJ; vol. 93/1, 1993, p. 2801.
Vidal, J.C, et al., "A Chronoamperometric Sensor for Hydrogen Peroxide Based on Electron Transfer Between Immobilized Horseradish Peroxidase on a Glassy Carbon Electrode and a Diffusing Ferrocene Mediator", Sensors and Actuators B:Chemical, vol. 21, Issue 2, Aug. 1994, pp. 135-141.
Patent Abstracts of Japan, JP A 59/3345, p-269, p. 166 (Hitachi Seisakusho K.K.) Jan. 10, 1994.
Hubbard, et al. The Theory and Practice of Electrochemistry with Thin Layer Cellls, in *Electroanalytical Chemistry*, (Bard, Ed.), Marcel Deletier, New York, 1970, vol. 4 (pp. 129-214).
Cassidy, et al.; "Novel Electrochemical Device for the Detection of Cholesterol or Glucose"; Analyst, vol. 118; Apr. 1993; pp. 415-418.
Christensen & Anson: "*Chronopotentiometry in Thin Layers of Solution*"; Analytical Chemistry, vol. 35; No. 2, 1963, pp. 205-209.
Hubbard & Anson; "*New Electrodes for Chronopotentiometry in Thin Layers of Solution*"; Analytical Chemistry, vol. 36, No. 4, Apr. 1964, pp. 723-728.
McDuffie, Anderson, & Reilley; "*Twin Electrode Thin-Layer Electrochemistry*"; Analytical Chemistry; vol. 38, No. 7, Jun. 1966; pp. 883-890.
Nicholson and Shain: "*Theory of Stationary Electrode Polarography*"; Analytical Chemistry: vol. 36, No. 4, Apr. 1964, pp. 706-723.
Pickup, Kutner, Leidner, and Murray; *Redox Conduction in Single and Bilayer Films of Redox Polymer*; J. Amer. Chem. Soc.; vol. 106; No. 7; 1984.

(56) References Cited

OTHER PUBLICATIONS

Chidsey, Feldman, Lundgren, and Murray; "*Micrometer-Spaced Platinum Interdigitated Array Electrode: Fabrication, Theory, and Initial Use*"; Analytical Chemistry, vol. 58, No. 3, Mar. 1986, pp. 801-807.

Anderson, McDuffie and Reilley; "*Diagnostic Criteria for the Study of Chemical and Physical Processes by Twin-Electrode Thin-Layer Electrochemistry*"; J. Electroanalytical Chemistry; vol. 12, 1966, pp. 477-494.

Hubbard; "*Study of the Kinetics of Electrochemical Reactions by Thin-Layer Voltammetry*"; J. Electroanalytical Chemistry, vol. 22, 1969, pp. 165-174.

Anderson and Reilley; "*Thin-Layer Electrochemistry: Steady-State Methods of Studying Rate Processes*"; J. Electroanalytical Chemistry; vol. 10, 1965, pp. 295-305.

Patent Abstracts of Japan, JP 08062179A; *Electrolyte Analyzer*; (Mar. 8, 1996).

Reilley, Charles; "*Electrochemistry Using Thin-Layer Cells*"; Review of Pure and Appl. Chem, vol. 18, 1968, pp. 137-151.

Morris, Franta and White; "*Electrochemistry at Pt Band Electrodes of Width Approaching Molecular Dimensions. Breakdown of Transport Equations at Very Small Electrodes*"; J. of Physical Chemistry, vol. 91, No. 13, 1987, pp. 3559-3564.

Derwent Abstract Accession No. 92 119462/15, Class S03, JP,A, 04-62463 (Tokyo Yogyo K.K.) Feb. 27, 1992.

Patent Abstracts of Japan, P-269. p. 166, JP, A,59/3345 (Hitachi Seisakusho K.K.) Jan. 10, 1994.

Hubbard, et al., The Theory and Practice of Electrochemistry with Thin Layer Cells, in *Electroanalytical Chemistry*, (Bard Ed.), Marcel Deletier, New York, 1970, vol. 4 (pp. 129-214).

Specification sheet from Adhesives Research, Inc., ARclad08314 (May 2, 1997).

Specification sheet from Adhesives Research, Inc., ARcare®4148 (Mar. 30, 1995) (2 pages).

Patent Abstract of Japanese Patent No. 63-139246 A2 (date Jun. 1988).

Data Sheet for ARcare 7148 double-side adhesive coated polyester film.

Abstract of Japanese Patent 0 0531 2761 A2; 1993; Y. Fukuda, et al.

Cassidy, et al.; "*Novel Electrochemical Device for the Detection of Cholesterol or Glucose*", vol. 118; Analyst, Apr. 1993; pp. 415-418.

Reilly, Charles; "*Electrochemistry Using Thin-layer Cells*", Rev. Pure and Appl. Chem., vol. 18, 1968; pp. 137-151.

Christensen & Anson; "*Chronopotentiometry in Thin Layers of Solution*"; Analytical Chemistry; vol. 35; No. 2, 1963, pp. 205-209.

Hubbard & Anson; "*New Electrodes for Chronopotentiometry in Thin Layers of Solution*", Analytical Chemistry; vol. 36, No. 4, Apr. 1964; pp. 723-726.

McDuffie, Anderson, & Reilly, "*Twin Electrode Thin-Layer Electrochemistry*"; Analytical Chemistry; vol. 38; No. 7; Jun. 1966; pp. 883-890.

Morris, Franta, and White: "*Electrochemistry at Pt Band Electrodes of Width Approaching Molecular Dimensions. Breakdown of Transport Equestions at Very Small Electrodes*"; The Journal of Physical Chemistry , vol. 91; No. 13; 1987; 3559-3564.

Nicholson and Shain; "*Theory of Stationary Electrode Polarography*"; Analytical Chemistry; vol. 36; No. 4, Apr. 1964; pp. 706-723.

Pickup, Kutner, Leidner, and Murray; "*Redox Conduction in Single and bilayer Films of Redox Polymer*"; American Chem. Society; vol. 106; No. 7; 1984.

Chidsey, Feldman, Lundgren, and Murray "*Micrometer-Spaced Platinum Interdigitated Array Electrode: Fabrication, Theory, and Initial Use*", Analytical Chemistry; vol. 58; No. 3; Mar. 1986;; 801-807.

Anderson, MdDuffie, Reilley; "*Diagnostic Criteria for the Study of Chemical and Physical Processes by Twin-Electrode Thin-Layer Electrochemistry*"; Journal of Electroanalytical Chemistry; vol. 12; 1966; 477-494.

Hubbard; "*Study of the Kinetics of Electrochemical Reactions by Thin-Layer Voltammetry*"; Journal of Electroanalytical Chemistry; vol. 22; 1969; pp. 165-174.

Anderson and Reilley; "*Thin-Layer Electrochemistry: Steady-State Methods of Studying Rate Processes*"; vol. 10; 1965; pp. 295-305.

Abstracts of Japan; Title: Electrolyte Analyzer; Publication No. 08062179 A (Mar. 8, 1996).

Abstract; JP 5312761A2; Title: Biosensor and Its Manufacture; Nov. 23, 1993.

Patent Abstract of Japan vol. 17, No. 258 (P-1540), May 20, 1993 JP 05 002007 A.

Patent Abstract of Japan vol. 17, No. 194 (P-1522), Apr. 15, 1993 JP 04 343065 A.

EP Search Report 03 00 7604, May 19, 2003.

JPO English language abstract of Kawaguri et al. JP 63-317097 A , patent published Dec. 26, 1988.

"Enthone—Imaging Technologies Update" Jun. 2001/No. 3.

Japanese Office Action for Japanese Application No. 2003-535271 dated Jul. 23, 2010 (3 pages).

Patent family history and equivalent filing s for WO 97/00441 A1 downloaded from Derwent on Mar. 4, 2011.

JPO computer generated English language translation of Japanese Patent Applciation Publication 2001-281219, downloaded on Feb. 28, 2011.

* cited by examiner

ELECTROCHEMICAL CELL

RELATED APPLICATIONS

This application claims priority as a continuation application to a utility application entitled "Electrochemical Cell" having application Ser. No. 12/567,433 filed on Sep. 25, 2009, now U.S. Pat. No. 8,101,056, which is a continuation of application Ser. No. 10/624,795 filed on Jul. 22, 2003, now U.S. Pat. No. 7,608,175, which is a continuation of application Ser. No. 10/035,924, filed Dec. 21, 2001, now U.S. Pat. No. 6,960,289, which is a continuation of application Ser. No. 09/618,515, filed Jul. 18, 2000, now U.S. Pat. No. 6,413,410, which is a continuation of application Ser. No. 08/981,385, filed Apr. 17, 1998, now U.S. Pat. No. 6,284,125, which is the national phase filing under 35 U.S.C. §371 of PCT International Application No. PCT/AU96/00365, which has an International filing date of Jun. 19, 1996, which designated the United States of America, which was published by the International Bureau in English on Jan. 3, 1997, and which claims priority to Australian Provisional Application No. PN 3639, filed Jun. 19, 1995.

FIELD OF THE INVENTION

This invention relates to a biosensor and more particularly to an electrochemical biosensor for determining the concentration of an analyte in a carrier. The invention is particularly useful for determining the concentration of glucose in blood and is described herein with reference to that use but it should be understood that the invention is applicable to other analytic determinations.

BACKGROUND OF THE INVENTION

Electrochemical biosensors generally comprise a cell having a working electrode, a counter electrode and a reference electrode. Sometimes the function of the counter and reference electrodes are combined in a single electrode called a "counter/reference" electrode or "pseudo reference electrode". As herein used the term "counter electrode" includes a counter/reference electrode where the context so admits.

The sample containing the analyte is brought into contact with a reagent containing an enzyme and a redox mediator in the cell. Either the mediator is reduced (receives at least one electron) while the analyte is oxidised (donates at least one electron) or visa versa. Usually it is the analyte which is oxidised and the mediator which is reduced. The invention will be herein described principally with reference to that system but it is also applicable to systems in which the analyte is reduced and the mediator oxidised.

Electrochemical glucose analysers such as those used by diabetics to monitor blood glucose levels or such as are used in clinics and hospitals are commonly based upon the use of an enzyme such as glucose oxidase dehydrogenase (GOD) and a redox mediator such as a ferricyanide or ferrocyanide. In such prior art system, the sample (e.g. blood) containing the analyte (e.g. glucose) is brought into contact with the reagents in the cell. Glucose is oxidised to gluconic acid and the glucose oxidase is thereby reduced. The mediator then re-oxidizes the glucose oxidase and is reduced in the process. The reduced mediator is then re-oxidized when it transfers electrons to the working electrode. After allowing passage of a predetermined time, sufficient to obtain an accurate estimate of the Faraday current, the concentration of glucose is estimated from the magnitude of the current or voltage signal then measured.

Prior art electrochemical cells consist of two (or three) adjacent electrodes spaced apart on one side of an insulator and adapted for connection to a measuring device. A target area on which the bipod sample is placed is defined on or between the electrodes. Co-pending Application PCT/AU95/00207 describes a cell in which electrodes are disposed on opposite sides of a porous membrane, one of the electrodes having a liquid permeable target area.

In the prior art there is a need to separate the working electrode from the counter (or counter/reference) electrode by a sufficient distance to avoid products of electrochemical reaction at one electrode from interfering with those at the other. In practice a separation of the electrodes of more than 500 μm is required to achieve acceptable accuracy.

Each batch of cells is required to have been previously calibrated and leads to inaccuracies during use because of variations within the batch, in sample composition, and in ambient conditions.

It is desired to improve, the accuracy and reliability of such biosensors. Achievement of these objectives is made difficult in the case of sensors intended to determine the concentration of analytes in blood because blood contains dissolved gases, ions, colloids, complex micelles, small scale cellular debris, and living cellular components in a predominantly aqueous medium. Any of these may interfere in the determination. Existing sensors are also susceptible to influence from other interfering substances that may be present in the sample and which may be oxidised at the working electrode and mistakenly identified as the analyte of interest. Alternatively, the interfering substances may reduce the oxidised form of the redox mediator. These effects will give artificially elevated estimates of the analyte concentration. Additionally there is always some reduced redox mediator present before the analyte is added and its concentration needs to be known and subtracted from the measured value of reduced mediator to give an accurate concentration of the analyte. Moreover, oxygen in the blood may act as a redox mediator for glucose oxidase dehydrogenase (GOD) in competition with ferrocyanide. Thus high oxygen concentrations can lead to low estimates of glucose concentration. In addition the measurements are sensitive to factors such as changes in humidity, temperature, solution viscosity and haematocrit content.

OBJECT OF THE INVENTION

It is an object of the present invention to provide a method of analysis and apparatus for use in the method which avoid or ameliorate at least some of the disadvantages of the prior art It is an object of preferred forms of the invention to provide a biosensor of improved accuracy, and/or reliability and/or speed and a method for its use.

DISCLOSURE OF THE INVENTION

According to one aspect the invention consists in a method for determining the concentration of a reduced (or oxidised) form of a redox species in an electrochemical cell of the kind comprising a working electrode and a counter electrode spaced from the working electrode by a predetermined distance, said method comprising the steps of:

(1) applying an electric potential difference between the electrodes, (2) selecting the potential of the working electrode such that the rate of electro-oxidation of the reduced form (or electro-reduction of the oxidised form) of the species is diffusion controlled, (3) selecting the spacing between the working electrode and the counter electrode so that reaction products from the counter electrode arrive at the working electrode, (4) determining current as a function of time after application of the potential and prior to achievement of a steady state, (5) estimating the magnitude of the steady state current, and (6) obtaining from the change in current with time and the magnitude of th steady state current, a value indicative of the diffusion coefficient and/or of the concentration of the reduced form (or the oxidised form) of the species.

The concentration measured in this way is substantially independent of variation if any in the diffusion coefficient of the reduced form, and therefore is compensated for variations in temperature and viscosity. The concentration so measured is independent of variations in haematocrit and other substances which affect the diffusion coefficient of the reduced form of the redox species.

It will be appreciated that the method; of the invention is equally applicable for determining the concentration of a reduced form of a redox species or an oxidized form of a redox species in the cell. In the case that the concentration of the reduced form is to be determined the potential of the working electrode must be maintained such that the rate of electro oxidation of the reduced form is diffusion controlled in step (2) and it is the concentration of the reduced form that is obtained in step (5). In the case that the concentration of oxidized form is to be determined, the potential of the working electrode must be maintained such that the rate of electro reduction of the oxidized form is diffusion controlled in step (2) and it is the concentration of the oxidized form that is obtained in step (5).

The redox species may be an analyte or may be a redox mediator.

In preferred embodiments of the method a mediator is used and the concentration of the reduced (or oxidized) form of the mediator is in turn indicative of the concentration of an analyte and a measure of the diffusion coefficient of the reduced (or oxidized) form of the mediator is determined as a precursor to the determination of the concentration of the analyte.

For preference the cell comprises a working electrode and counter/reference electrode. If a reference electrode separate from a counter electrode is used, then the reference electrode may be in any convenient location in which it is in contact with the sample in the sensor.

In contrast to prior art, when conducting the method of the invention, the electrodes are sufficiently close that the products of electrochemical reaction at the counter electrode migrate to the working electrode during the period of the test. For example, in an enzyme ferricyanide system, the ferrocyanide produced at the counter electrode diffuses to the working electrode.

This allows a steady state concentration profile to be achieved between the electrodes leading to a steady state current. This in turn allows the diffusion coefficient and concentration of the redox species (mediator) to be measured independently of sample variations and therefore greatly improves accuracy and reliability.

The method also permits the haematocrit concentration of blood to be determined from the diffusion coefficient by use of look-up tables (or by separation of red cells from plasma and measurement of the diffusion coefficient of the red cell fraction) and the plasma fraction, and comparing the two.

According to a second aspect, the invention consists in apparatus for determining the concentration of a redox species in an electrochemical cell comprising:

an electrochemical-cell having a working electrode and a counter (or counter/reference) electrode, means for applying an electric potential difference between said electrodes, means for measuring the change in current with time, and characterised in that the working electrode is spaced from the counter electrode by less than 500 μm.

In preferred embodiments the cell has an effective volume of 1.5 microliters or less. Apparatus for use in the invention may comprise a porous membrane, a working electrode on one side of the membrane, a counter/reference electrode on the other side, said electrodes together with a zone of the membrane therebetween defining an electrochemical cell, and wherein the membrane extends laterally from the cell to a sample deposition area spaced apart from the cell zone by a distance greater than the thickness of the membrane.

Preferably the porous membrane, the distance of the target area from the cell portion, and the membrane thickness are so selected in combination that when blood (comprising plasma and red cells) is placed on the target area a plasma front diffuses laterally towards the electrochemical cell zone in advance of the red cells.

It is thus possible to fill a thin layer electrochemical cell with plasma substantially free of haematocrit which would cause a variation in the diffusion coefficient of the redox mediator and which would affect the accuracy of the test as hereinafter explained.

In preferred embodiments of the biosensor according to the invention a second electrochemical cell zone of the membrane is defined by a second working electrode and a second counter/reference electrode on the opposite side of the membrane from the second working electrode. The second electrochemical cell zone is situated intermediate the first cell zone and the sample deposition or "target" area, or is situated on the side of the target area remote from the first electrochemical zone. In these embodiments the plasma comes into contact with enzyme in, or on route to, the first electrochemical cell while plasma reaching the second cell does not. The first cell thus in use measures the concentration of reduced mediator in the presence of plasma (including electrochemically interfering substances), and enzyme while the second electrochemical cell measures it in the presence of plasma (including electrochemically interfering substances) and in the absence of enzyme. This allows determination of the concentration of the reduced interfering substances in the second cell and the concentration of reduced interfering substances plus analyte in the first cell. Subtraction of the one value from the other gives the absolute concentration of analyte.

In a highly preferred embodiment of the invention a hollow cell is employed wherein the working and reference (or counter/reference) electrodes are spaced apart by less than 500 μm and preferably by from 20-200 μm.

DESCRIPTION OF THE DRAWINGS

The invention will now be more particularly described by way of example only with reference to the accompanying drawings wherein:

In FIGS. 5 to 12, components corresponding in function to components of the embodiment of FIGS. 1 to 4 are identified by identical numerals or indicia.

DESCRIPTION OF PREFERRED EMBODIMENTS

Figure 1:
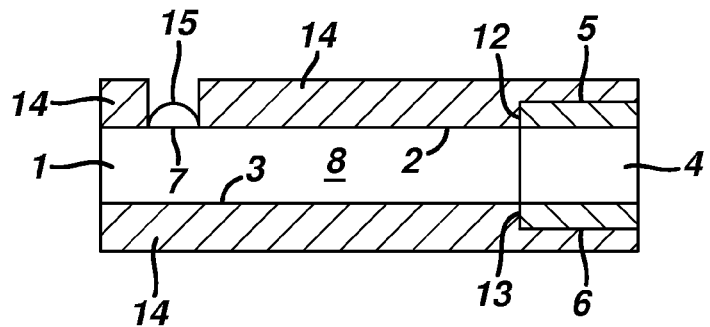
FIG. 1 is a schematic drawing (not to scale) of a first embodiment, according to the invention shown in side elevation.
Figure 2:
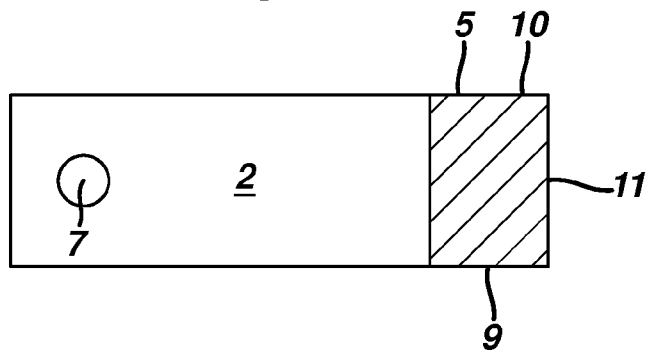
FIG. 2 shows the embodiment of FIG. 1 in plan, viewed from above.
Figure 3:
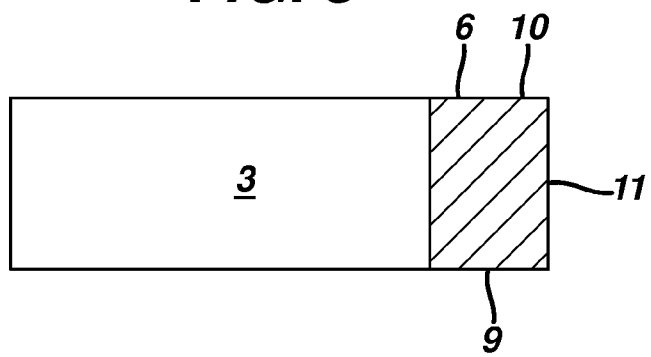
FIG. 3 shows the embodiment of FIG. 1 in plan, viewed from below.
Figure 4:
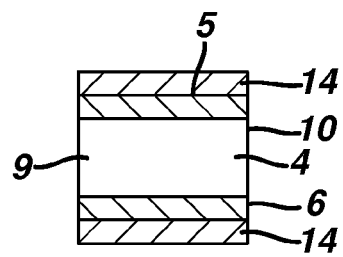
FIG. 4 shows the embodiment of FIG. 1 viewed in end elevation.

With reference to FIGS. 1 to 4 there is shown a first embodiment of apparatus of the invention, in this case a biosensor for determining glucose in blood. The embodiment comprises a thin strip membrane 1 having upper and lower surfaces 2, 3 and having a cell zone 4 defined between a working electrode 5 disposed on upper surface 2 and a counter electrode 6 disposed on lower surface 3. The membrane thickness is selected so that the electrodes are separated by a distance "l" which is sufficiently close that the products of electrochemical reaction at th counter electrode migrate to the working electrode during the time of the test and a steady state diffusion profile is substantially achieved. Typically, "l" will be less than 500 μm. A sample deposition or "target" area 7 defined on upper surface 2 of membrane 1 is spaced at a distance greater than the membrane thickness from cell zone 4. Membrane 1 has a diffusion zone 8 extending between target area 7 and cell zone 4. A suitable reagent including a redox mediator "M", an enzyme "E" and a pH buffer "B" are contained within cell zone 4 of the membrane and/or between cell zone 4 and target area 7. The reagent may also include stabilisers and the like.

In some cases it is preferable to locate the enzyme and mediator and/or the buffer in different zones of the membrane. For example the mediator may be initially located within electrochemical cell zone 4 while the enzyme may be situated below target area 7 or in diffusion zone 8.

Haemoglobin releases oxygen at low pH's, but at higher pH's it binds oxygen very firmly. Oxygen acts as a redox mediator for glucose oxidase dehydrogenase (GOD). In a glucose sensor this competes with the redox mediator leading to low estimates of glucose concentration. Therefore if desired a first pH buffer can be contained in the vicinity of target area 7 to raise the pH to such a level that all the oxygen is bound to haemoglobin. Such a pH would be non-optimal for GOD/glucose kinetics and would consequently be detrimental to the speed and sensitivity of the test. In a preferred embodiment of the invention a second pH buffer is contained as a reagent in the vicinity of the working electrode to restore the pH to kinetically optimal levels. The use of a second buffer does not cause oxygen to be released from the haemoglobin as the haemoglobin is contained within the blood cells which are retained near blood target area 7 or are retarded in diffusion in comparison with the plasma and therefore not influenced by the second buffer. In this manner oxygen interference may be greatly reduced or eliminated.

In use of the sensor a drop of blood containing a concentration of glucose to be determined is placed on target zone 7. The blood components wick towards cell zone 4, the plasma component diffusing more rapidly than red blood cells so that a plasma front reaches cell zone 4 in advance of blood cells.

When the plasma wicks into contact with the reagent, the reagent is dissolved and a reaction occurs that oxidises the analyte and reduces the mediator. After allowing a predetermined time to complete this reaction an electric potential difference is applied between the working electrode and the counter electrode. The potential of the working electrode is kept sufficiently anodic such that the rate of electro oxidation of the reduced form of the mediator at the working electrode is determined by me rate of diffusion of the reduced form of the mediator to the working electrode, and not by the rate of electron transfer across the electrode/solution interface.

In addition the concentration of the oxidised form of the mediator at the counter electrode is maintained at a level sufficient to ensure that when a current flows in the electrochemical cell the potential of the counter electrode, and thus also the potential of the working electrode, is not shifted so far in the cathodic direction that the potential of the working electrode is no longer in the diffusion controlled region. That is to say, the concentration of the oxidized form at the counter electrode must be sufficient to maintain diffusion controlled electro oxidation of the reduced form of the mediator at the working electrode.

The behaviour of a thin layer cell is such that if both oxidised and reduced forms of the redox couple are present, eventually a steady state concentration profile is established across the cell. This results in a steady state current. It has been found that by comparing a measure of the steady state current with the rate at which the current varies in the current transient before the steady state is achieved, the diffusion coefficient of the redox mediator can be measured as well as its concentration. This is in contrast to the Cottrell current that is measured in the prior art. By measuring the Cottrell current at known times after application of a potential to the sensor electrodes it is only possible to determine the product concentration times square root of the diffusion coefficient and therefore it is not possible to determine the concentration of the mediator independent of its diffusion coefficient.

In a cell according to the current invention, by solving the appropriate diffusion equations it can be shown that over a restricted time range a plot of $\ln(i/i^\infty - 1)$ vs time (measured in seconds) is linear and has a slope (denoted by S) which is equal to $-4\pi^2 D/l^2$, where "i" is the current at time "t", "$i^\infty$" is the steady state current, "D" is the diffusion coefficient in cm$^2$/sec, "l" is the distance between the electrodes in cm and "π" is approximately 3.14159. The concentration of reduced mediator present when the potential was applied between the electrodes is given by $2\pi^2 i^\infty FAlS$, where "F" is Faraday's constant, A is the working electrode area and the other symbols are as given above. As this later formula uses S it includes the measured value of the diffusion coefficient.

Since l is a constant for a given cell, measurement of i as a function of time and $i^\infty$ enable the value of the diffusion coefficient of the redox mediator to be calculated and the concentration of the analyte to be determined.

Moreover the determination of analyte concentration compensates for any variation to the diffusion coefficient of the species which is electro oxidised or electro reduced at the working electrode. Changes in the value of the diffusion coefficient may occur as a result of changes in the temperature and viscosity of the solution or variation of the membrane permeability. Other adjustments to the measured value of the concentration may be necessary to account for other factors such as changes to the cell geometry, changes to the enzyme chemistry or other factors which may effect the measured concentration. If the measurement is made on plasma substantially free of hematocrit (which if present causes variation in the diffusion coefficient of the redox mediator) the accuracy of the method is further improved.

Each of electrodes 5, 6 has a predefined area. In the embodiments, of FIGS. 1 to 4 cell zone 4 is defined by edges 9, 10, 11 of the membrane which correspond with edges of electrodes 5, 6 and by leading (with respect to target area 7) edges 12, 13 of the electrodes. In the present example the electrodes are about 600 angstrom thick and are from 1 to 5 mm wide.

Optionally, both sides of the membrane are covered with the exception of the target area 7 by laminating layers 14 (omitted from plan views) which serves to prevent evaporation of water from the sample and to provide mechanical robustness to the apparatus. Evaporation of water is undesirable as it concentrates the sample, allows the electrodes to dry out, and allows the solution to cool, affecting the diffusion coefficient and slowing the enzyme kinetics, although diffusion coefficient can be estimated as above.

Figure 5:
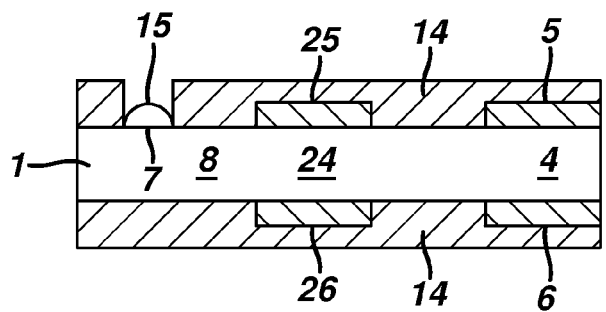
FIG. 5 is a schematic drawing (not to scale) of a second embodiment according to the invention in side elevation.
Figure 6:
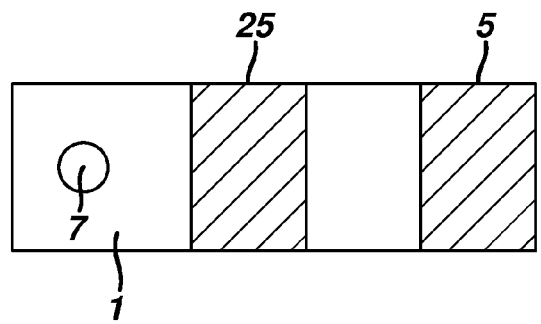
FIG. 6 shows the embodiment of FIG. 5 in plan, viewed from above.

A second embodiment according to the invention, shown in FIGS. 5 and 6, differs from the first embodiment by inclusion of a second working electrode 25 and counter/reference electrode 26 defining a second cell zone 24 therebetween. These electrodes are also spaced apart by less than 500 μm in the present example. Second electrodes 25, 26 axe situated intermediate cell zone 4 and target area 7. In this embodiment the redox mediator is contained in the membrane below or adjacent to target area 7 or intermediate target area 7 and first cell zone 4. The enzyme is contained in the membrane in the first cell zone 4 and second cell zone 24. The enzyme does not extend into second cell 24. In this case when blood is added to the target area, it dissolves the redox mediator. This wicks along the membrane so that second electrochemical cell 24 contains redox mediator analyte and serum including electrochemically interfering substances. First electrochemical cell receives mediator, analyte, serum containing electrochemically interfering substances, and enzyme. Potential is now applied between both working electrodes and the counter electrode or electrodes but the change in current with time is measured separately for each pair. This allows the determination of the concentration of reduced mediator in the absence of analyte plus the concentration of electrochemically interfering substances in the second electrochemical cell and the concentration of these plus analyte in me first electrochemical cell. Subtraction of the one value from the other gives the absolute concentration of analyte.

Figure 7:
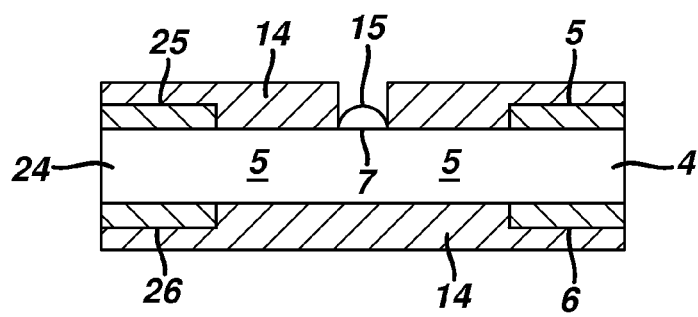
FIG. 7 is a schematic drawing (not to scale) of a third embodiment according to the invention, in side elevation.
Figure 8:
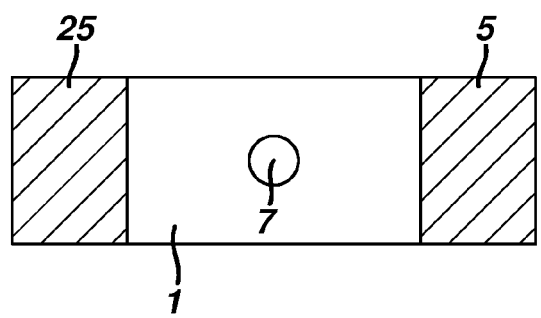
FIG. 8 shows the embodiment of FIG. 7 in plan, viewed from above.

The same benefit is achieved by a different geometry in the embodiment of FIGS. 7 and 8 in which the second working electrode and second counter/reference electrode define me second cell 24 on me side of target area 7 remote from first electrochemical cell 4. In this case the enzyme may be contained in the membrane strip between the target area and cell 1. The redox mediator may be in the vicinity of the target area or between the target area and each cell. The diffusion coefficient of mediator is lowered by undissolved enzyme and the arrangement of FIGS. 7 and 8 has the advantage of keeping enzyme put of the thin layer cells and allowing a faster test (as the steady state current is reached more quickly). Furthermore the diffusion constant of redox mediator is then the same in both thin layer cells allowing more accurate subtraction of interference.

Figure 9:
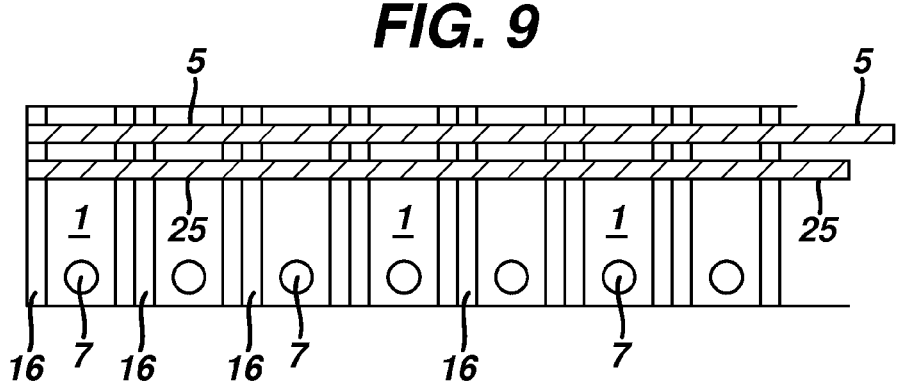
FIG. 9 is a schematic drawing (not to scale) according to the invention in plan view, viewed from above.
Figure 10:
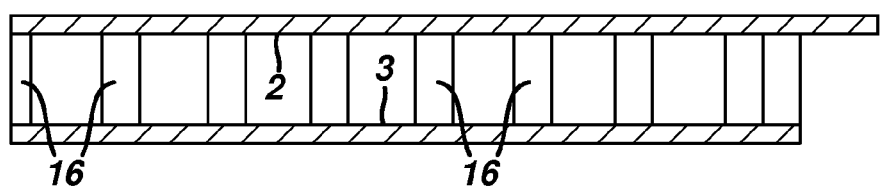
FIG. 10 shows the embodiment of FIG. 9 in end elevation.
Figure 11:
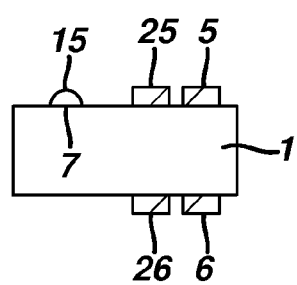
FIG. 11 shows me embodiment of FIG. 9 in side elevation.

Although the embodiments of FIGS. 1 to 8 are unitary sensors, it will be understood that a plurality of sensors may be formed on a single membrane as shown in the embodiment of FIGS. 9 to 11. In this case the electrodes of one sensor are conductively connected to those of an adjacent sensor. Sensors may be used successively and severed from the strip after use.

In the embodiment of FIGS. 9 to 11 electrode dimensions are defined in the diffusion direction (indicated by arrow) by the width of the electrode in that direction. The effective dimension of the electrode in a direction transverse to diffusion direction is defined between compressed volumes 16 of the membrane in a manner more fully described in co-pending Application PCT/AU96/00210, the disclosure of which is incorporated herein by reference in its entirety. For clarity optional laminated layer 14 of FIG. 1 has been omitted from FIGS. 9 to 11.

Figure 12:
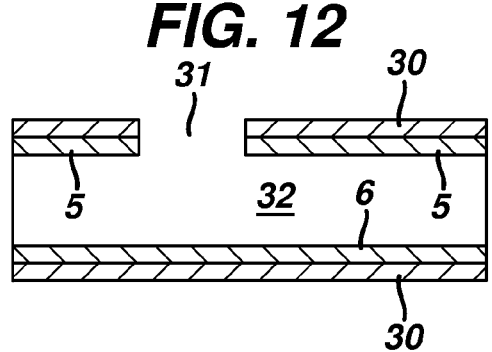
FIG. 12 shows a schematic drawing (not to scale) of a hollow cell embodiment according to the invention, viewed in cross section.

In the embodiment of FIG. 12 there is shown a hollow cell according to the invention wherein the electrodes 5, 6 are supported by spaced apart polymer walls 30 to define a hollow cell. An opening 31 is provided on one side of the cell whereby a sample can be admitted into cavity 32. In this embodiment a membrane is not used. As in previous embodiments, the electrodes are spaced apart by less than 500 μm, preferably 20-400 μm and more preferably 20-200 μm. Desirably the effective cell volume is 1.5 microliters or less.

It will be understood that the method of the invention may be performed with a cell constructed in accord with co-pending application PCT/AU95/00207 or cells of other known design, provided these are modified to provide a sufficiently small distance between electrode faces.

Figure 13:
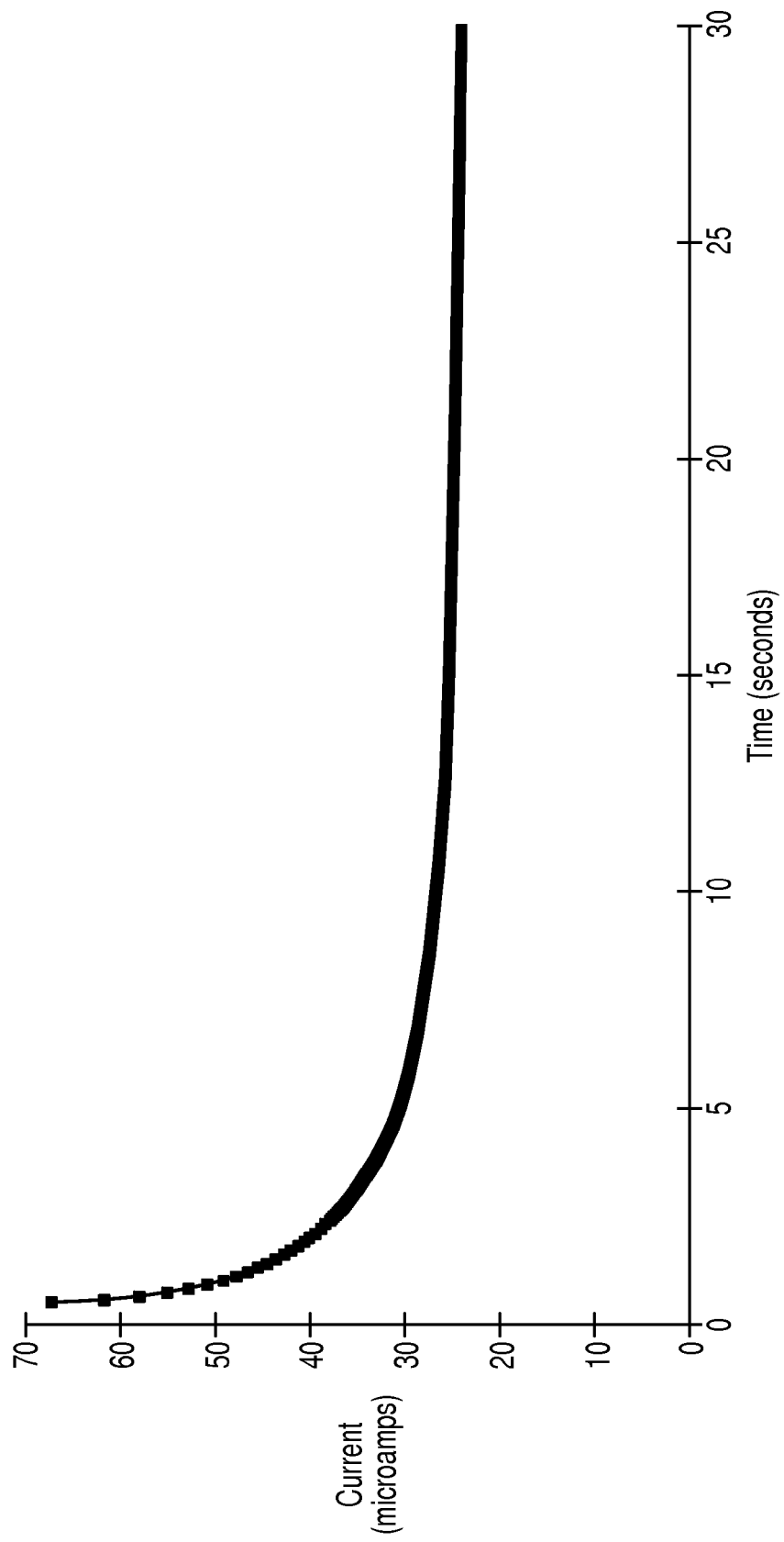
FIG. 13 is a graph showing a plot of current (ordinate axis) versus time (co-ordinate axis) during conduct of a method according to the invention.
Figure 14:
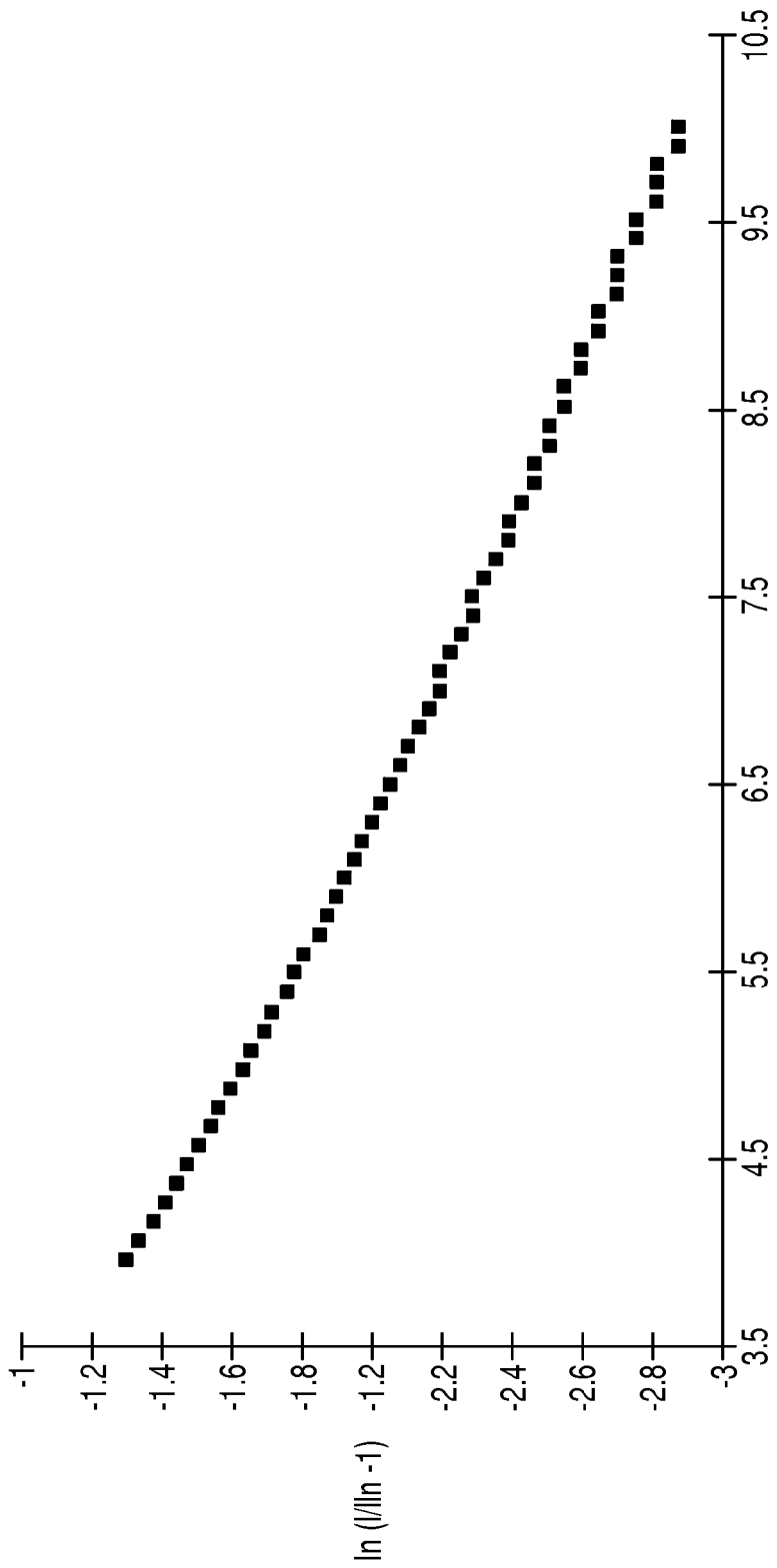
FIG. 14 is a further graph of use in explaining the method of the invention.

The method of the invention will now be further exemplified with reference to FIGS. 13 and 14.

Example 1

A membrane 130 microns thick was coated on both sides with a layer of Platinum 60 nanometers thick. An area of 12.6 sq. mm was defined by impressing the membrane. 1.5 microliters of a solution containing 0.2 Molar potassium ferricyanide and 1% by weight glucose oxidase dehydrogenase was added to the defined area of the membrane and the water allowed to evaporate.

The platinum layers were then connected to a potentiostat to be used as the working and counter/reference electrodes. 3.0 microliters of an aqueous solution containing 5 millimolar D-glucose and 0.9 wt % NaCl was dropped on to the defined area of the membrane. After an elapse of 20 seconds a voltage of 300 millivolts was applied between the working and counter/reference electrodes and the current recorded for a further 30 seconds at intervals of 0.1 seconds.

FIG. 13 is a graph of current versus time based on the above measurements. Using a value of the steady state current of 26.9 microamps the function $\ln(i/26.9-1)$ was computed and plotted versus time. The slope of the graph (FIG. 14) is $-0.342$ which corresponds to a diffusion coefficient of $1.5 \times 10^{-6}$ cm$^2$ per second and a corrected glucose concentration (subtracting background ferrocyanide) of 5.0 millimolar.

The steady state current is one in which no further significant current change occurs during the test. As will be understood by those skilled in the art, a minimum current may be reached after which there may be a drift due to factors such as lateral diffusion, evaporation, interfering electrochemical reactions or the like. However, in practice it is not difficult to estimate the "steady state" current ($i^\infty$). One method for doing so involves approximating an initial value for $i^\infty$. Using the fit of the i versus t data to the theoretical curve a better estimate of $i^\infty$ is then obtained. This is repeated reiteratively until the measured value and approximated value converge to within an acceptable difference, thus yielding an estimated $i^\infty$.

In practice, the measurements of current i at time t are made between a minimum time t min and a maximum time t max after the potential is applied. The minimum and maximum time are determined by the applicability of the equations and can readily be determined by experiment of a routine nature. If desired the test may be repeated by switching off the voltage and allowing the concentration profiles of the redox species to return towards their initial states.

It is to be understood that the analysis of the current v. time curve to obtain values of the Diffusion Co-efficient and/or concentration is not limited to the method given above but could also be achieved by other methods.

For instance, the early part of the current v. time curve could be analysed by the Cottrell equation to obtain a value of $D^{1/2} \times Co$ (Co=Concentration of analyte) and the steady state current analysed to obtain a value of $D \times Co$. These 2 values can then be compared to obtain D and C separately.

It will be understood that in practice of the invention an electrical signal is issued by the apparatus which is indicative of change in current with time. The signal may be an analogue or digital signal or may be a series of signals issued at predetermined time intervals. These signals may be processed by means of a microprocessor or other conventional circuit to perform the required calculations in accordance with stored algorithms to yield an output signal indicative of the diffusion coefficient, analyte concentration, haematocrit concentration or the like respectively. One or more such output signals may be displayed by means of an analogue or digital display.

It is also possible by suitable cell design to operate the cell, as a depletion cell measuring the current required to deplete the mediator. For example in the embodiment of FIG. 5 the method of the invention may be performed using electrodes 5, 6, which are spaced apart by less than 500 µm. An amperometric or voltametric depletion measurement may be made using electrodes 5 and 26 which are spaced apart more than 500 µm and such that there is no interference between the redox species being amperometrically determined at electrodes 5, 26.

The depletion measurement may be made prior to, during or subsequent to, the measurement of diffusion coefficient by the method of the invention. This enables a substantial improvement in accuracy and reproducibility to be obtained.

In the embodiments described the membrane is preferably an asymmetric porous membrane of the kind described in U.S. Pat. No. 4,629,563 and U.S. Pat. No. 4,774,039 both of which are incorporated herein in their entirety by reference. However symmetrical porous membranes may be employed. The membrane may be in the form of a sheet, tube, hollow fibre or other suitable form.

If the membrane is asymmetric the target area is preferably on the more open side of the asymmetric membrane. The uncompressed membrane desirably has a thickness of from 20 to 500 µm. The minimum thickness is selected having regard to speed, sensitivity, accuracy and cost. If desired a gel may be employed to separate hematocrit from GOD. The gel may be present between the electrodes and/or in the space between the sample application area and the electrodes.

The working electrode is of any suitable metal for example gold, silver, platinum, palladium, iridium, lead, a suitable alloy. The working electrode may be preformed or formed in situ by any suitable method for example sputtering, evaporation under partial vacuum, by electrodeless plating, electroplating, or the like. Suitable non-metal conductors may also be used for electrode construction. For example, conducting polymers such as poly(pyrrole), poly(aniline), porphyrin "wires"; poly(isoprene) and poly (cis-butadiene) doped with iodine and "ladder polymers". Other non-metal electrodes may be graphite or carbon mixed with a binder, or a carbon filled plastic. Inorganic electrodes such as $In_2O_3$ or $SnO_2$ may also be used. The counter/reference electrode may for example be of similar construction to the working electrode. Nickel hydroxide or a silver halide may also be used to form the counter/reference electrode. Silver chloride may be employed but it will be understood that chloridisation may not be necessary and silver may be used if sufficient chloride ions are present in the blood sample. Although in the embodiments described the working electrode is shown on the upper surface of the biosensor and the counter/reference electrode is on the lower surface, these may be reversed.

It is preferable that the working electrode and counter (or counter/reference) electrodes are of substantially the same effective geometric area.

If a separate reference and counter electrode are employed, they may be of similar construction. The reference electrode can be in any suitable location.

It will be understood that the features of one embodiment herein described may be combined with those of another. The invention is not limited to use with any particular combination of enzyme and mediator and combinations such as are described in EP 0351892 or elsewhere may be employed. The system may be used to determine analytes other than glucose (for example, cholesterol) by suitable adaptation of reagents and by appropriate membrane selection. The system may also be adapted for use with media other than blood. For example the method may be employed to determine the concentration of contaminants such as chlorine, iron, lead, cadmium, copper, etc., in water.

Although the cells herein described have generally planar and parallel electrodes it will be understood that other configurations may be employed, for example one electrode could be a rod or needle and me other a concentric sleeve.

It will be apparent to those skilled in the art from the disclosure hereof the invention may be embodied in other forms without departing from the inventive concept herein disclosed.

The invention claimed is:

1. A hollow electrochemical cell comprising:
   a cell housing defined by spaced apart walls including an opening in one of said walls for the admission of a quantity of sample;
   a pair of electrodes comprising a working electrode and a counter electrode at least partially facing each other in a diffusion zone within the interior of said cell between said spaced apart walls and downstream of said opening in which sample flows under capillary action through said diffusion zone from said opening towards said pair of electrodes; and
   at least one additional electrode disposed in the diffusion zone and upstream of the working electrode and the counter electrode with respect to a sample flow through the diffusion zone.

2. The hollow electrochemical cell of claim 1, wherein the additional electrode is co-planar with the counter electrode.

3. The hollow electrochemical cell of claim 2, wherein the additional electrode is an additional working electrode.

4. The hollow electrochemical cell of claim 1, wherein the additional electrode is co-planar with the working electrode.

5. The hollow electrochemical cell of claim 4, wherein the additional electrode is an additional working electrode.

6. A hollow electrochemical cell comprising:
- a cell housing defined by spaced apart walls including an opening in one of said walls for the admission of a quantity of sample;
- a pair of electrodes comprising a working electrode and a counter electrode at least partially facing each other in a diffusion zone within the interior of said cell between said spaced apart walls and downstream of said opening in which sample flows under capillary action through said diffusion zone from said opening towards said pair of electrodes;
- two additional electrodes disposed in the diffusion zone and at a predetermined distance from the working electrode and the counter electrode; and
- at least one of the two additional electrodes being disposed upstream of the working electrode and the counter electrode with respect to a sample flow through the diffusion zone.

7. The hollow electrochemical cell of claim 6, wherein the predetermined distance is less than 500 μm.

* * * * *